United States Patent [19]
Thor et al.

[11] Patent Number: 5,580,349
[45] Date of Patent: Dec. 3, 1996

[54] BLOOD RESERVOIR

[75] Inventors: Eric J. Thor, Columbia Heights; Kevin D. McIntosh, Albertville; Theresa M. Schaefer, Plymouth, all of Minn.

[73] Assignee: Avecor Cardiovascular, Inc., Plymouth, Minn.

[21] Appl. No.: 123,364

[22] Filed: Sep. 17, 1993

[51] Int. Cl.⁶ .................................................. A61M 1/36
[52] U.S. Cl. ............................ 604/406; 604/4; 604/324; 604/403; 604/408; 422/44
[58] Field of Search ...................... 604/4–6, 317, 604/324, 403, 406, 408; 128/DIG. 24; 422/44–45, 47–48

[56] References Cited

U.S. PATENT DOCUMENTS

| | | |
|---|---|---|
| 2,570,639 | 10/1951 | Cahan . |
| 2,599,738 | 6/1952 | Ames . |
| 2,981,253 | 4/1961 | Wall et al. ................................ 422/45 |
| 3,205,889 | 9/1965 | Alder et al. . |
| 3,730,835 | 5/1973 | Leeper et al. . |
| 3,788,369 | 1/1974 | Killinger . |
| 3,985,135 | 10/1976 | Carpenter et al. . |
| 4,026,669 | 5/1977 | Leonard et al. . |
| 4,035,304 | 7/1977 | Watanabe ................................ 604/406 |
| 4,191,231 | 5/1980 | Winchell et al. . |
| 4,196,088 | 4/1980 | Bacehowski et al. . |
| 4,235,233 | 11/1980 | Mouwen . |
| 4,424,190 | 1/1984 | Mather, III et al. . |
| 4,437,472 | 3/1984 | Naftulin . |
| 4,466,888 | 8/1984 | Verkaart . |
| 4,484,920 | 11/1984 | Kaufman et al. . |
| 4,493,705 | 1/1985 | Gordon et al. . |
| 4,507,114 | 3/1985 | Bohman et al. . |
| 4,600,613 | 7/1986 | Yoshida . |
| 4,645,482 | 2/1987 | Yoshida . |
| 4,717,377 | 1/1988 | Fukasawa . |
| 4,734,269 | 3/1988 | Clarke et al. . |
| 4,790,815 | 12/1988 | Balteau et al. . |
| 4,795,457 | 1/1989 | Cooney . |
| 4,854,737 | 8/1989 | Steer et al. . |
| 4,863,452 | 9/1989 | Irmiter et al. . |
| 4,876,788 | 10/1989 | Steer et al. . |
| 4,910,147 | 3/1990 | Bacehowski et al. . |
| 4,959,062 | 9/1990 | Gellman . |
| 4,976,708 | 12/1990 | Oshiyama ................................ 604/4 |
| 5,061,236 | 10/1991 | Sutherland et al. . |
| 5,126,175 | 6/1992 | Yamakoshi . |
| 5,135,600 | 8/1992 | Ishida . |
| 5,209,347 | 5/1993 | Fabisiewicz et al. . |

*Primary Examiner*—Randall L. Green
*Assistant Examiner*—P. Zuttarelli
*Attorney, Agent, or Firm*—Popovich & Wiles, P.A.

[57] ABSTRACT

An improved blood reservoir formed by opposed, flexible sheets has a screen sandwiched between the sheets defining an input chamber, an output chamber, and vent chamber. A vent is in fluid communication with the vent chamber. An outlet is in fluid communication with the output chamber. One or more inlets direct blood into the input chamber through apertures that direct blood upward and along the screen, allowing gas bubbles entrained in the blood to escape through the vent. Support springs around the inlets allow them to be flexed without kinking. The reservoir can be coupled to an improved mounting board for use.

20 Claims, 5 Drawing Sheets

BLOOD RESERVOIR

FIELD OF THE INVENTION

The present invention relates to an improved blood reservoir for use in the medical field. In particular, the present invention relates to a blood reservoir for use in extracorporeal blood oxygenation systems.

BACKGROUND OF THE INVENTION

As part of various surgical procedures, an extracorporeal blood circuit is used to temporarily collect blood drained from the patient and return the blood to the patient prior to completion of the procedure. The blood reservoir may store venous blood and cardiotomy blood. For cardiovascular surgical procedures cardiopulmonary bypass systems are utilized to perform blood oxygenation and circulatory support while normal cardiopulmonary function of a patient is interrupted or impaired. A cardiopulmonary bypass system typically includes an oxygenation device for oxygenating blood before it is returned to the patient, a heat exchanger to regulate blood temperature, a pump to regulate the flow of blood, and a blood reservoir for collecting blood.

The cardiopulmonary bypass system usually collects two types of blood from the patient: venous blood, collected through the patient's vascular system, and cardiotomy blood, suctioned from the surgical site. Different tubing and filters may be used when drawing these two types of blood from the patient, but venous and cardiotomy blood are usually combined prior to reinfusion into the patient by a common line.

It is critical that air or gas bubbles entrained in the venous and cardiotomy blood are removed prior to reinfusing the blood into the patient. Air bubbles introduced into the patient's vascular system may occlude the capillaries of various organs of the patient resulting in various life-threatening conditions. The air bubbles can be of various sizes ranging from bubbles visible to an observer to tiny micro-emboli that can pass through fine mesh screens and are difficult to detect. Since there may be no filters in the bypass system between the output of the blood reservoir and the patient, it is essential that the blood reservoir remove gas bubbles, including micro-emboli. Also, it is important that the blood reservoir minimize stagnation of the blood.

Prior art blood reservoirs have assumed various shapes and incorporated various filters and vent tubes for removing air bubbles. For example, U.S. Pat. No. 4,734,269 disclosed a flexible-bag reservoir having an inlet on the bottom of the bag expelling blood into an envelope-like filter. Other examples of blood reservoirs are disclosed in U.S. Pat. Nos. 5,061,236, 4,795,457, and 4,493,705.

It is apparent that although the prior art devices provide some bubble removal, there remains a need for more effective gas bubble removal, particularly for the above-described micro-emboli. Further, there remains a need for such a blood reservoir with an improved blood flow performance to reduce blood stagnation in the reservoir.

SUMMARY OF THE INVENTION

In accordance with the present invention, a blood reservoir is provided wherein first and second opposed, flexible sheets are sealed together along their respective edges to define a sealed bag. A screen, such as a polyester mesh sheet, is disposed between the flexible sheets and is connected to one of the flexible sheets along the lateral and bottom edges of the screen, covering substantially all of the inner surface of one of the sheets except for a portion at the bottom of the sheet and a portion at the top of the sheet, thereby defining an input chamber, an output chamber, and a common vent chamber for the bag.

A blood inlet is located on each of the lateral sides of the bag. Each blood inlet extends horizontally into the bag with apertures located on the top cross-section of the inlets directing all of the blood toward the top of the bag. These two inlets may be formed by a single tube extending through the bag from the first to the second lateral side, and having a wall blocking blood flow at some point intermediate the two lateral sides, thereby defining the two blood inlets. At least one vent tube is provided at the top of the bag in communication with the vent chamber. An infusion inlet, also in communication with the vent chamber, may be provided at the top of the bag for infusing therapeutic substances into the blood. Finally, an outlet is provided at the bottom of the bag.

In operation, blood is pumped into the bag through the inlet tubes and is directed upwardly through the apertures toward the top of the bag. The velocity of the blood exiting the first aperture is roughly equal to the velocity of blood exiting the other apertures. Under normal operating conditions, blood generally moves through a first venous inlet upward in a counterclockwise, sweeping motion, reaching an apex, then falling toward the bottom of the bag. Likewise, blood generally moves through a second cardiotomy inlet upward in a clockwise, sweeping motion, reaching an apex, then falling toward the bottom of the bag.

Typically, one of the inlets is for venous blood and the other inlet is for cardiotomy blood. In one embodiment, the horizontal length of the venous inlet is longer than the inlet for the cardiotomy blood. The venous inlet is larger because there is a relatively larger and constant flow of venous blood compared to cardiotomy blood.

Also, the size and location of the apertures perform an important function. Micro-emboli have a small buoyancy force with respect to the bubbles drag force and tend to be carried along by the blood flow. The apertures direct all of the blood from the inlets upward so that gas bubbles, including micro-emboli entrained in the blood, are also directed upward. When the blood then falls toward the bottom of the bag, the upwardly moving bubbles can escape and exit the bag through a vent. Therefore, the upward blood flow is important.

Further, the aperture configuration distributes the incoming blood minimizing turbulence. The apertures that are closer to the distal end of each of the inlets have a circumference smaller than the circumference of the apertures closer to the lateral edge of the bag. Therefore, the velocity of the blood exiting each of the apertures is reduced and is approximately the same. The result is a more uniform flow of blood upwardly, reducing shear forces and stagnant areas in the inlet. Also, a slower, more constant flow upward toward the vent at the top of the bag enhances separation of the bubbles from the blood. Finally, as the blood flows along the screen, the screen enhances bubble separation from the blood.

The blood reservoir of the present invention can be coupled to a mounting board which holds the reservoir in a vertical position. Vent mounts, inlet mounts, and an outlet mount selectively hold the respective vent, inlet and outlet tubes in a fixed position. Mounting pegs extend outward from the board for coupling the bag to the board through the reservoir's coupling apertures. Also, the mounting board includes a face plate which is placed parallel to the bag on the side of the bag opposite the board so that the bag lies between the mounting board and the face plate. The distance of the face plate from the mounting board can be adjusted, thus limiting the expansion of the bag as it collects blood, forcing the blood to flow upward. The face plate provides a blood path to the top of the bag at low reservoir volumes facilitating air removal.

Finally, inlet support means, such as helical springs or coils, are placed around a part of the inlet tubes extending away from the bag. The springs or coils have an inner diameter equal to or slightly larger than the outer diameter of the inlet tubes, thereby supporting the tubes if they are flexed in any direction and preventing kinking of the inlet tubes.

It is an object of the present invention to provide an improved blood reservoir.

It is another object of the present invention to provide a blood reservoir with an improved gas debubbling capability.

It is another object of the present invention to provide a blood reservoir where blood is directed into the reservoir upward at a constant velocity along a screen in order to enhance debubbling.

It is another object of the present invention to provide a blood reservoir having inlet and outlet tubes that can be flexed in various directions without crimping.

It is another object of the present invention to provide a blood reservoir with a mounting board which holds the blood reservoir in an upright position for effective operation and limits expansion of reservoir.

It is another object of the present invention to provide a blood reservoir having a mounting board and a face plate whereby the expansion of the blood reservoir can be controlled.

DETAILED DESCRIPTION OF THE PREFERRED EMBODIMENT

Figure 1:
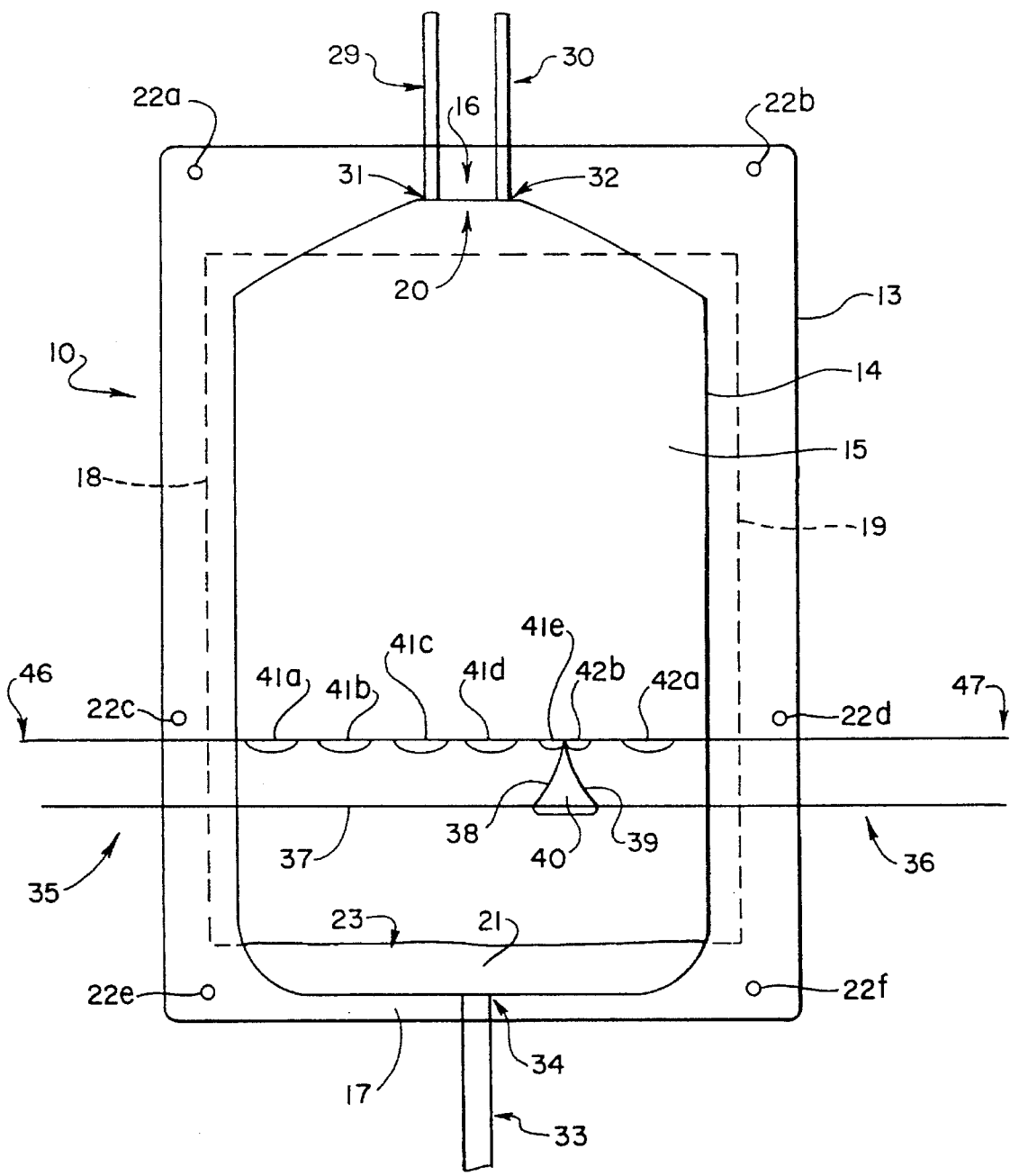
FIG. 1 is a front view of the blood reservoir of the present invention.

The following detailed description and the accompanying drawings are provided for the purpose of describing an embodiment of the invention and are not intended to limit the scope of the invention in any way.

Referring to FIGS. 1–4, the blood reservoir 10 of the present invention is shown. The reservoir 10 is formed of a first 11 and a second 12 sheet of flexible material. Typically, the material is a polyvinyl chloride sheet, 0.020"±0.001" in thickness, matte finish on both sides, medical grade 100% virgin material, e.g., ES3000, available from Ellay. The first 11 and second 12 sheets are situated in surface-to-surface juxtaposition and are sealed or connected along their selected boundaries. In the embodiment of the invention shown in FIG. 1, sheets 11 and 12 are sealed together at two boundaries. A first, outermost seal 13 connects the outer edges of rectangular sheets 11 and 12. A second, inner seal 14 defines the rounded-corner, inner shape of the bag. Typically, the sheets 11 and 12 are sealed together by radio frequency welding; however, impulse sealing or other heat sealing methods can be used.

The connected sheets 11, 12 define a bag having an expandable blood collecting inner volume 15. Also, the bag has a top 16, a bottom 17, and first and second lateral sides 18 and 19, when the bag is positioned in an upright, vertical position during use. Lateral sides 18 and 19 are generally straight and parallel to each other. Lateral sides 18, 19 are longer than top 16 and bottom 17. Top 16 is formed by opposed upward curves from each lateral side that flatten out to form a flat uppermost portion 20. Bottom 17 is formed by opposed downward curves from each lateral side that flatten out to form a lowermost flat portion 21. In the embodiment of FIG. 1, the uppermost 20 and lowermost 21 portions are shown to be in the center of the bag, i.e., equidistant from lateral edges 18 and 19; however, uppermost 20 and lowermost 21 portions may be displaced along the top and bottom side, respectively, in alternate embodiments. The reservoir 10 includes mounting apertures 22a–f for connecting reservoir 10 to a mounting board discussed further below.

In one embodiment of the invention, blood reservoir 10 has a maximum volume of 1250 ml and a standard operating volume of 1000 ml. In an alternate embodiment, blood reservoir 10 has a smaller volume, e.g. 500 ml, for pediatric applications.

A porous screen or filter 25 is positioned within the inner volume 15 for enhancing the gas bubble removal from the blood. In the preferred embodiment, screen 25 is made of medical grade, PeCap polyester having a mesh aperture of 105 µm, a thread diameter of 40 µm, and a fabric thickness of 61 µm. As shown by the dotted lines in FIGS. 1 and 2, the screen 25 is fixed between sheets 11 and 12 along lateral sides 8 and 19, and connected to sheet 11 along the bottom edge of screen 23. Screen 25 can be welded to first sheet 11 by radio frequency welding or other connecting methods discussed above. In an alternate embodiment, the screen 25 is welded to the first sheet 11 along the entire edge of the screen.

Figure 2:
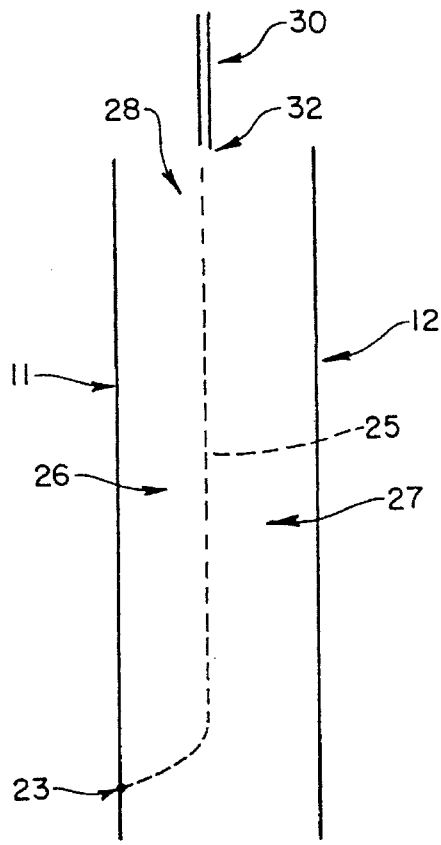
FIG. 2 is an exploded side view of the blood reservoir of the present invention.

As shown in FIG. 2, screen 25 is parallel to and sandwiched between the opposed surfaces of first and second sheets 11, 12. As shown in FIG. 1, screen 25 extends from the first lateral side 18 to the opposed second lateral side 19 and is sealed to the first sheet 11 approximately 1½" above the lowermost portion 21 of the bag. The top edge of the screen is not sealed to first sheet 11 and extends toward the top side of the bag approximately ⅜" below the uppermost portion 20. The resulting configuration of the inner volume 15 is an inlet chamber 26 disposed between first sheet 11 and screen 25, an adjacent output chamber 27 between second screen 12 and screen 25, and a vent chamber 28 at the top of the bag in fluid communication with both the input chamber 26 and output chamber 27. The input chamber 26 and output chamber 27 are in fluid communication through screen 25.

At the uppermost portion 20 of reservoir 10, a vent 29 is provided for venting air or gas bubbles released from the blood. A second vent 30 is spaced laterally from first vent 29. The second vent 30 may also function as an infusion means for infusing therapeutic substances, such as medicine or other supplements, into the blood. Vent means 29 and 30 are formed by medical PVC with a ¼" inner diameter and ¹/₁₆" wall thickness, sealed between sheets 11 and 12, having a distal end 31 and 32, respectively, flush with or recessed above the uppermost portion 20 of the inner volume 15. Vents 29, 30 are in fluid communication with vent chamber 28; therefore, gas bubbles escaping from either the input 26 or output 27 chamber can pass into vent chamber 28 and out of the reservoir 10 through vent 29 or 30. Of course, if only one vent is being used, the gas bubbles will escape through that vent.

At the lowermost portion 21 a blood outlet 33 is provided. The blood outlet means 33 is typically a medical PVC tube having a ⅜" inner diameter and ¹/₁₆" wall thickness. The distal end 34 of blood outlet tube 33 is flush with or recessed below the lowermost portion 21 to reduce or eliminate any areas for blood stagnation. As in the case of the vent tubing, the outlet tube diameter is typical of those currently used in cardiopulmonary bypass systems; however, other sized tubing may be used.

Disposed on first 18 and second 19 lateral sides are blood inlet means 35 and 36, respectively. In the embodiment shown in FIG. 1, first and second inlet means 35, 36 are formed by a single tube 37 extending horizontally through the bag from first lateral side 18 to second lateral side 19. Tubular member 37 has an inner diameter of ½" with a ³/₃₂" wall thickness. Tube 37 extends into the bag between sheets 11, 12 on both first and second lateral sides 18, 19. Sheets 11, 12 are sealed to the outer circumference of tube 37 to prevent blood leaking from the bag.

Referring to the side view of blood reservoir 10 shown in FIG. 2, the tube 37 is disposed between first sheet 11 and screen 15 in the input chamber 26. The screen 15 is connected to first sheet 11 below tube 26.

Figure 3:
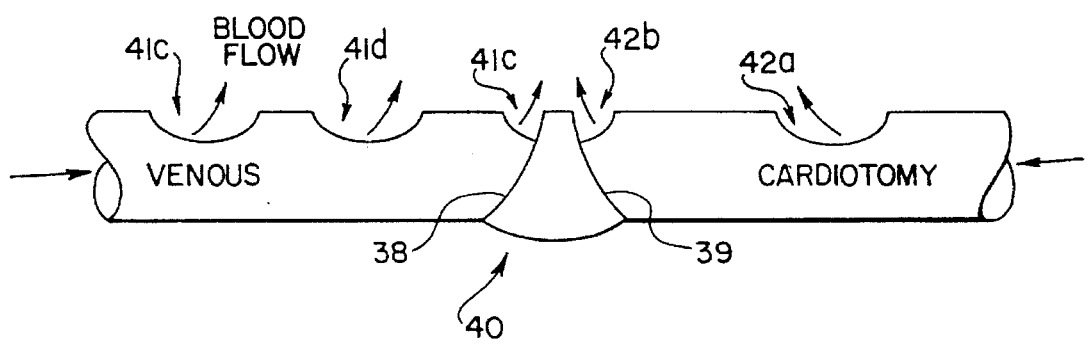
FIG. 3 is a side view of the inlet means of the blood reservoir.

As shown in FIGS. 1 and 3, tube 37 is completely closed at a point between first and second lateral sides 18 and 19. This closure forms closed distal ends 38 and 39 for inlet means 35 and 36, respectively. This closure or wall 40 can be formed by heat sealing the tube closed. The heat seal creates a slope on sides 38 and 39 of wall means 40, the downward slope in each case being away from the distal end of the respective inlet means. The slope directs blood passing through tube 37 toward the apertures (discussed below) and eliminates stagnant areas.

In an alternate embodiment of the invention, inlet means 35 and 36 are not formed by a single tube, rather they are formed by separate tubes having closed distal ends and apertures.

Tube 37 includes a series of apertures facing the top of the bag. Apertures 41a–e are in communication with inlet means 35 and apertures 42a–b are in communication with inlet means 36. The apertures are linearly spaced along the top half of the cross-section of tube 37. Apertures 41c–e are smaller than apertures 41a, 41b. In the preferred embodiment of the invention, apertures 41a, 41b have a generally oval shape with a maximum length of 0.625" and a width of 0.375", aperture 41c has a maximum length of 0.5" and maximum width of 0.25", aperture 41d has a maximum length of 0.375" and width of 0.25". Aperture 41e is smaller than apertures 41a–d and is formed by the heat seal of the tube 37 in the middle of an aperture.

For inlet means 36, aperture 42a is approximately 0.625" by 0.375", and aperture 42b is approximately the same size as aperture 41e. Also, the length of inlet means 36 extending horizontally into inlet chamber 26 is shorter than the length of inlet means 35 extending into the inlet chamber 26. In the preferred embodiment, inlet means 36 extends approximately 1½" into inlet chamber 26 and inlet means 35 extends approximately 4" into the inlet chamber 26. The difference in number of apertures and the length of the inlet means extending into the input chamber is due to the fact that inlet means 35 is typically used for venous blood and inlet means 36 is typically used for cardiotomy blood.

Generally, venous blood will be continuously pumped in through inlet means 35 and the configuration described above allows for a maximum venous inlet flow rate of approximately seven liters per minute. Cardiotomy blood is typically pumped in through inlet means 36 on an episodic or sporadic basis requiring a lower rate. However, during emergency procedures the amount of cardiotomy blood may increase rapidly; therefore, in the embodiment described above, the cardiotomy inlet 36 is capable of handling three to four liters of blood per minute.

As shown in FIG. 1, inlet means 35 and 36 each include a tubular portion extending away from lateral sides 18 and 19, respectively. In one embodiment, the inlet means extend at least three inches away from lateral edges 18 and 19, respectively, terminating in proximal ends 46 and 47. A ½" by ½" polycarbonate straight connector is attached to proximal end 46 with two lure lock fittings. At the proximal end 47 of inlet means 36 for cardiotomy inlet flow, is a polycarbonate Y connector, with a ½" base and ⅜" and ¼" barbed connections. Although inlet means 36 has an inner diameter of ½", cardiopulmonary bypass systems typically have a ⅜" cardiotomy line. Therefore, there is a necessity for the ½ to ⅜" reducer. The ¼" barb is used to connect the reservoir to recirculation lines.

Figure 4:
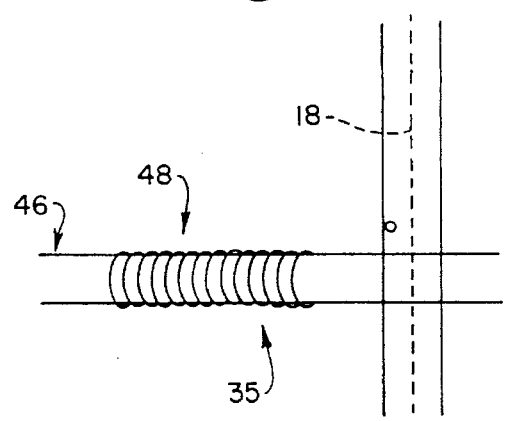
FIG. 4 is a side view of a support means of the blood reservoir.

Disposed toward proximal ends 46 and 47 of inlet means 35 and 36, a coaxial support means surrounds the outer surface of inlet means 35 and 36. Support means 48 for inlet means 35 is shown in FIG. 4. Support means for inlet means 36 and outlet means 33 are of a similar construction. In the preferred embodiment, support means 48 is a stainless steel helical spring coated with polyurethane or epoxy. The inner diameter of the helical spring 48 is equal to or slightly larger than the outer diameter of inlet means 35. The helical spring allows the flexible tubing of inlet means 35 and 36 to be flexed in various directions without the tube crimping. At the point where a tube crimps, the cross-sectional area of the tube is decreased, changing the blood flow rate; therefore, crimping can not only affect the operation of blood reservoir 10, but also the entire bypass system. The support means 48 is also used in conjunction with the mounting board discussed further below. Also, the support means 48 is spaced toward the distal end of the inlet means, leaving a gap adjacent the lateral side where a clamp can control the flow of blood into the reservoir.

Blood reservoir 10 can be attached to a mounting board 50 during use. Referring to FIGS. 5a–e, planar mounting board 50 is made of a polycarbonate material, 15" tall with an upper portion 7½" wide and a lower portion 10.1/4" wide. Extending from mounting board 50 are coupling means or pegs 51a–f for holding blood reservoir 10 generally parallel to and adjacent to mounting board 50. Pegs 51a–f are spaced about the periphery of a first side of board 50 to match with the connecting holes 22a–f in blood reservoir 10. In the embodiment shown in FIG. 5a, upper pegs 51a, 51b at the top of the mounting board are approximately 5½" apart and one inch from the lateral edge of the board. These upper pegs extend approximately ⅞" to 1" out from board 50. Intermediate pegs 51c, 51d also extend orthogonally approximately 1⅝" from mounting board 50. Lower pegs 51c, 51f are spaced approximately 6" apart and are spaced inwardly from the lateral edge approximately 2¼". Lower pegs 51d, 51f extend orthogonally 1¼" from mounting board 50. As shown in FIG. 5b, pegs 51a–f have a cylindrical stem 52 and a cap 53 having a circumference wider than the circumference of the cylindrical stem. When blood reservoir 10 is connected to mounting board 50 by pegs 51a–f, the bag is slightly stretched in order to pull the holes over the caps 53 and slide down onto the stem 52 of the pegs. As the bag fills with blood, the bag can move along shafts 52; however, caps 53 prevent the holes from sliding off of the bag.

Vent tube holder 54 is located at the top center of the first side of mount board 50 for holding vent tubes in a fixed position. The vent holder is made of polycarbonate or other suitable material and is attached to the board 50 via adhesive, bolts, or other widely-known fasteners. The vent mount means 54 includes two recessed areas 55, 56 each for receiving a vent 29, 30, respectively. The neck width 57 of recessed areas 55, 56 is smaller than the outer diameter of vent tubes 29 and 30. The inner, cylindrical area of recessed areas 55, 56 has a diameter equal to the outer diameter of vent tubes 29, 30. Therefore, the vents snapped into the inner recessed areas are unlikely to accidentally fall out.

Inlet mounts 57, 58 are also made of polycarbonate or other suitable material and are attached to the first side of board 50 by any one of the connecting methods identified above or generally known in the art. As shown in FIG. 5d, inlet mounts 57, 58 have a general "c" shape as they extend away from mount board 50. The inlet mount means has a bore 59 for receiving the blood inlet means and associated support means of blood reservoir 10. The bore 10 includes an inner lip 60 with a diameter equal to the outer diameter of blood inlet means 35 or 36, whereas the remaining portion of the bore has a larger diameter 61 equal to the outer diameter of support means 48.

When mounting blood reservoir 10 to mounting board 50, support springs 48 are compressed and pulled towards the proximal ends 46 and 47, respectively, and the inlet means are placed in the bore. Once the inlet means are placed in the bore, springs 48 are released and expand until they meet inner lip of 60. In this configuration, the support means 48 not only performs the function of preventing kinking of the inlet means as they are flexed, but also serve to pull the proximal ends of the inlet tubes taut and prevent the inlet means from being pulled out of the inlet mounts 57, 58 without compressing the support spring 48.

Immediately adjacent the inlet mounts 57, 58 are clamp slots 62, 63. In one embodiment, the slots are 1¾" long and ½" wide. Slots 62, 63 allow for rapid clamping of the inlet means 35, 36 immediately adjacent lateral sides 18, 19 by use of a hemostat clamp or other clamp means without the inconvenience and limitation of the ends of the hemostat or clamp hitting the board 50.

At the bottom of the first side mounting board 50 an outlet mount and face plate support 64 is provided. The outlet mount means 65 is similar to the vent mount in that it includes a neck width narrower than the outer diameter of the outlet tube and a cylindrical, inner recess for receiving the outlet tube and having a diameter equal to the outer diameter of the outlet means. Therefore, the outlet tube is snapped into the outlet mount and cannot easily be removed therefrom. In an alternate embodiment, the outlet mount means 65 is of similar configuration as the inlet mount described above.

Lateral to each side of the outlet mount are cylindrical rods 66 extending across recessed areas 67. These cylindrical rods 66 will be discussed further below with respect to the face plate.

Figure 6A:
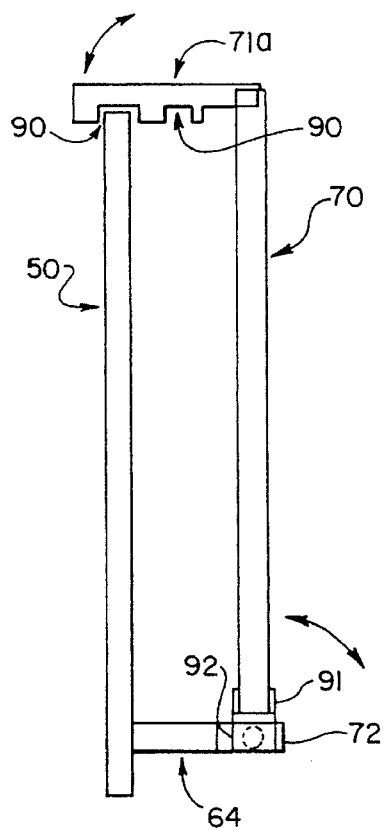
FIG. 6a is a side view of the face plate coupled to the mounting board.
Figure 6B:
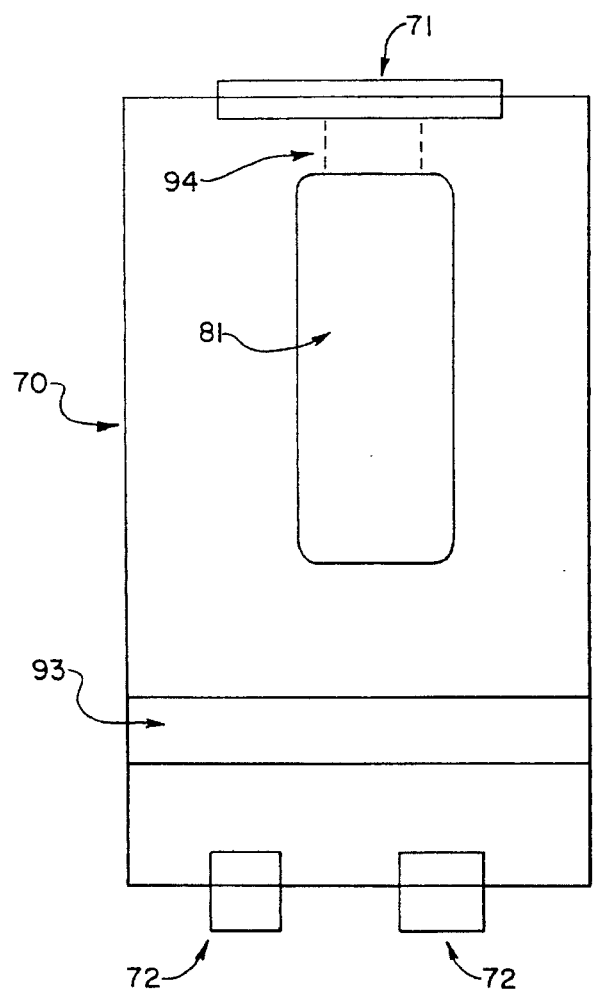
FIG. 6b is a front view of the face plate.

As shown in FIGS. 6a–b, a face plate 70 is connected to mounting board 50. Face plate 70 is made of polycarbonate or other suitable material and is removably coupled to board 50 by upper 71 and lower 72 coupling means.

Upper coupling means 71 is a U-shaped metal bar attached to face plate 70 by a pin hinge. As shown in FIG. 6a, the sides of the U-shaped bar have at least two recessed areas 90.

Lower coupling means 72 is a double U-shaped metal piece. The bottom edge of face plate 70 extends into the upward "U" 91 and is fixed by a suitable fastening method. The downward "U" 92 is open for coupling to mounting board 50.

The face plate is coupled to mounting board 50 by first placing the open, downward "U" 92 of the lower coupling means 72 over the cylindrical rods 66 of the face plate support 64. The length of the sides of the downward "U" 92 are such that the rods 66 act as a hinge allowing the top of face plate 70 to rotate away from the top of board 50.

Next, the upper coupling means 71 is rotated upward on its hinge and the top of face plate 70 is rotated toward board 50. The face plate 70 is coupled at a fixed distance from board 50 by rotating upper coupling means 71 downward so that one of recessed areas 90 fits over the top edge of mount board 50. The face plate 70 is fixed in place until upper coupling means 71 is rotated upward.

Figure 5A:
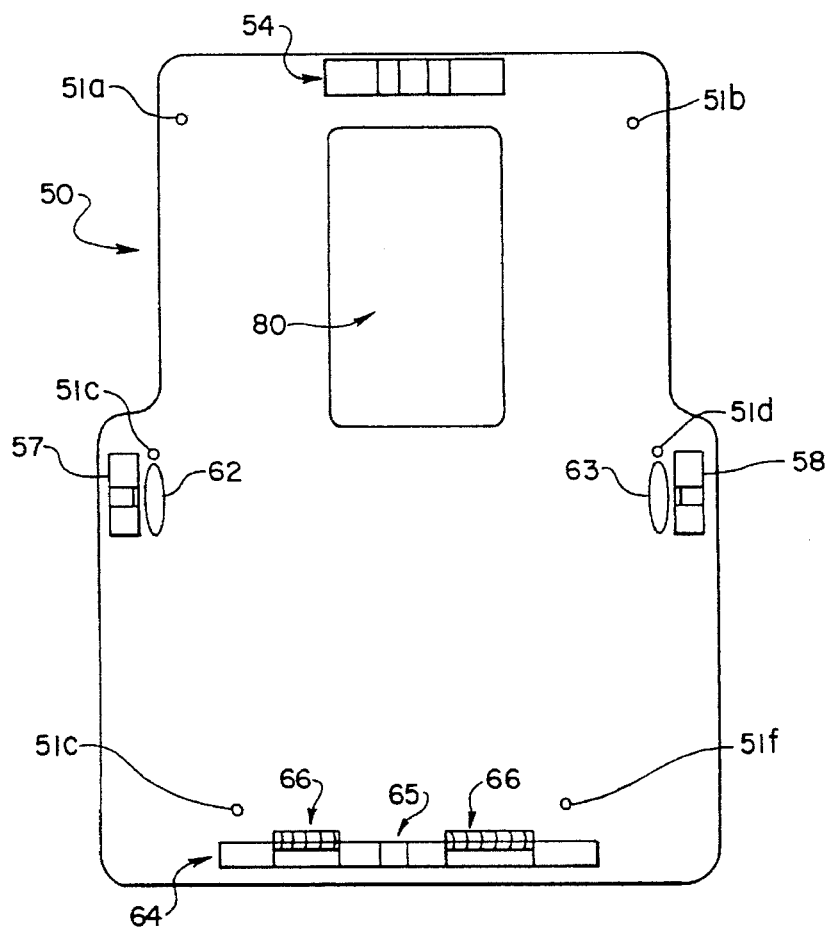
FIG. 5a is a front view of the mounting board of the present invention.
Figure 5B:
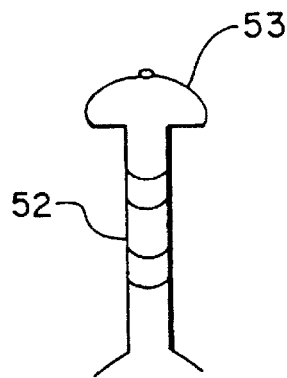
FIGS. 5b–e are a side view of the peg, vent support, inlet support, and outlet and face plate support features of the mounting board.
Figure 5C:
Figure 5D:
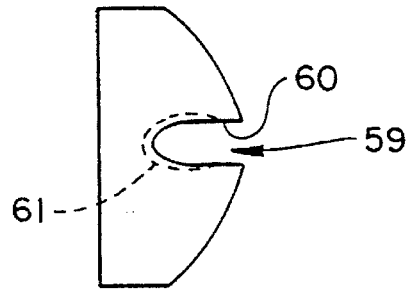
Figure 5E:
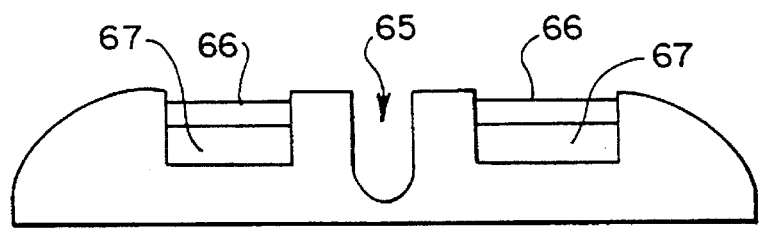

In the embodiment of the invention shown in FIGS. 5a and 6b, board 50 and face plate 70 have centrally disposed slots or apertures 80 and 81, respectively. When face plate 70 is coupled to mount board 50, a blood reservoir 10 disposed between them can expand only to the opposed surfaces of the face plate and board. The apertures 80, 81 allow some additional expansion in the central part of the bag. The result of this configuration is that blood entering the reservoir 10 is forced upward and to the center of the bag, maximizing the debubbling function. Also, face plate 70 includes a recessed groove 93 extending horizontally across the side of the face plate facing the reservoir to correspond with the inlet means 35,36 to avoid crimping them and restricting blood flow through the inlet means 35,36. finally, recessed area 94, above aperture 81, is provided to prevent occluding the vents 29,30 on the reservoir.

What is claimed is:

1. A blood reservoir, comprising:
    (a) first and second opposed, flexible sheets sealed together along their respective edges defining a sealed bag having an inner volume for receiving blood, said bag further having a top, a bottom, and first and second lateral sides when said bag is positioned upright during use;
    (b) a screen for removal of gas bubbles from blood, comprising a top edge, a bottom edge, and first and second lateral edges, said screen disposed between the first and second flexible sheets and connected to the first sheet along the bottom, first and second lateral edges of said screen, dividing the inner volume into an input chamber and an output chamber in fluid communication through said screen said screen being porous over substantially its entire surface;
    (c) a blood outlet provided at the bottom of the bag and in fluid communication with the output chamber; and
    (d) a first blood inlet provided at the first lateral side of the bag, said first blood inlet including a first tubular member extending horizontally from said first lateral side to the input chamber, said first tubular member having a closed distal end and one or more apertures located in the input chamber, said apertures facing the top of the bag.

2. The blood reservoir of claim 1 wherein the top edge of said screen is not attached to either first or second sheets, said inner volume further includes a vent chamber disposed above the input chamber and output chamber and in fluid communication with the input chamber and output chamber, and said blood reservoir further comprises a vent provided at the top of the bag and in fluid communication with the vent chamber.

3. The blood reservoir of claim 1 wherein the top edge of said screen is sealed to the first sheet, said inner volume further includes a vent chamber disposed above the input chamber and output chamber and in fluid communication with the input chamber and output chamber, and said blood reservoir further comprises a vent provided at the top of the bag and in fluid communication with the vent chamber.

4. The blood reservoir of claim 1 wherein the screen is a polyester mesh sheet.

5. A blood reservoir, comprising:
   (a) first and second opposed, flexible sheets sealed together along their respective edges defining a sealed bag having an inner volume for receiving blood, said bag further having a top, a bottom, and said first and second lateral sides when said bag is positioned upright during use;
   (b) a screen for removal of gas bubbles from blood, comprising a top edge, a bottom edge, and first and second lateral edges, said screen disposed between the first and second flexible sheets and connected to the first sheet along the bottom, first and second lateral edges of said screen, dividing the inner volume into an input chamber and an output chamber in fluid communication through said screen, wherein the top edge of said screen is not attached to either first or second sheets, said inner volume further includes a vent chamber disposed above the input chamber and output chamber and in fluid communication with the input chamber and output chamber;
   (c) a vent provided at the top of the bag and in fluid communication with the vent chamber;
   (d) a blood outlet provided at the bottom of the bag and in fluid communication with the output chamber;
   (e) a first blood inlet provided at the first lateral side of the bag, said first blood inlet including a first tubular member extending horizontally from said first lateral side to the input chamber, said first tubular member having a closed distal end and one or more apertures located in the input chamber, said apertures facing the top of the bag; and
   (f) an infusion tube provided at the top of the bag and in fluid communication with the vent chamber.

6. A blood reservoir comprising:
   (a) first and second opposed, flexible sheets sealed together along their respective edges defining a sealed bag having an inner volume for receiving blood, said bag further having a top, a bottom, and said first and second lateral sides when said bag is positioned upright during use;
   (b) a screen for removal of gas bubbles from blood, comprising a top edge, a bottom edge, and first and second lateral edges, said screen disposed between the first and second flexible sheets and connected to the first sheet along the bottom, first and second lateral edges of said screen, dividing the inner volume into an input chamber and an output chamber in fluid communication through said screen, wherein the top edge of said screen is not attached to either first or second sheets, said inner volume further includes a vent chamber disposed above the input chamber and output chamber and in fluid communication with the input chamber and output chamber;
   (c) a vent provided at the top of the bag and in fluid communication with the vent chamber;
   (d) a blood outlet provided at the bottom of the bag and in fluid communication with the output chamber;
   (e) a first blood inlet provided at the first lateral side of the bag, said first blood inlet including a first tubular member extending horizontally from said first lateral side to the input chamber, said first tubular member having a closed distal end and one or more apertures located in the input chamber, said apertures facing the top of the bag; and
   (f) a second blood inlet provided at the second lateral side of the bag, said second blood inlet including a second tubular member extending from said second lateral side horizontally into the input chamber, said second tubular member having a closed distal end and one or more apertures located in the input chamber, said apertures facing the top of the bag.

7. The blood reservoir of claim 6 wherein the first blood inlet receives venous blood and the second blood inlet receives cardiotomy blood.

8. The blood reservoir of claim 6 wherein there are a plurality of said apertures of the first and second tubular member and said apertures are linearly spaced.

9. The blood reservoir of claim 6 wherein the first tubular member and the second tubular member are a single tube extending through the input chamber from the first lateral side to the second lateral side, said tube including a wall disposed between the first lateral side and the second lateral side, said wall having a first side forming the closed distal end of the first tubular member and a second side forming the closed distal end of the second tubular member.

10. The blood reservoir of claim 6 wherein the first and second sides of said wall are sloped to direct blood toward said one or more apertures.

11. The blood reservoir of claim 8 wherein each of the plurality of apertures of the first tubular member have a circumference that is smaller than the circumference of the aperture adjacent to and closer to the first lateral side of the bag.

12. The blood reservoir of claim 8 wherein the first tubular member has five apertures, and the circumference of the two apertures closest to the first lateral side is larger than the circumference of the remaining three apertures.

13. The blood reservoir of claim 6 wherein the first tubular member extends into the input chamber a first distance, the second tubular member extends into the input chamber a second distance, and the first distance is greater than the second distance.

14. The blood reservoir of claim 6 wherein the first tubular member is flexible and has a proximal end extending away from the first lateral side of the bag and the second tubular member is flexible and has a proximal end extending away from the second lateral side of the bag.

15. The blood reservoir of claim 1 further comprising a first support coaxial with and surrounding a portion of the first tubular member disposed between the first lateral side of the bag and the proximal end of the first tubular member.

16. The blood reservoir of claim 6 further comprising a second support coaxial with and surrounding a portion of the second tubular member disposed between the second lateral side of the bag and the proximal end of the second tubular member.

17. The blood reservoir of claim 6 wherein the first inlet is located approximately ¼ of the distance from the bottom edge to the top edge of the bag on the first lateral side of the bag and the second inlet is located approximately ¼ of the distance from the bottom edge to the top edge of the bag on the second lateral side of the bag.

18. The blood reservoir of claim 6 further comprising a mount for holding the bag in a generally upright position, the mount including a generally planar board, a bag coupler connected to said board, a first clamp slot formed in said board for receiving a first clamp for controlling the flow of blood through the first inlet, a second clamp slot formed in said board through the second inlet, a first inlet mount connected to said board, a second inlet mount connected to said board, and a face plate parallel and connected to said board.

19. A blood reservoir, comprising:
 (a) first and second opposed, flexible sheets sealed together along their respective edges defining a sealed bag having an inner volume for receiving blood, said bag further having a top, a bottom, and first and second lateral sides when said bag is positioned upright during use;
 (b) a screen for removal of gas bubbles from blood, comprising a top edge, a bottom edge, and first and second lateral edges, said screen disposed between the first and second flexible sheets and connected to the first sheet along the bottom, first and second lateral edges of said screen, dividing the inner volume into an input chamber and an output chamber in fluid communication through said screen;
 (c) a blood outlet provided at the bottom of the bag and in fluid communication with the output chamber; and
 (d) a first blood inlet provided at the first lateral side of the bag, said first blood inlet including a first tubular member extending horizontally from said first lateral side to the input chamber, said first tubular member having a closed distal end and one or more apertures located in the input chamber, said apertures facing the top of the bag; and
 (e) an infusion tube provided at the top of the bag and in fluid communication with the vent chamber.

20. A blood reservoir, comprising:
 (a) first and second opposed, flexible sheets sealed together along their respective edges defining a sealed bag having an inner volume for receiving blood, said bag further having a top, a bottom, and first and second lateral sides when said bag is positioned upright during use;
 (b) a screen for removal of gas bubbles from blood, comprising a top edge, a bottom edge, and first and second lateral edges, said screen disposed between the first and second flexible sheets and connected to the first sheet along the bottom, first and second lateral edges of said screen, dividing the inner volume into an input chamber and an output chamber in fluid communication through said screen;
 (c) a blood outlet provided at the bottom of the bag and in fluid communication with the output chamber; and
 (d) a first blood inlet provided at the first lateral side of the bag, said first blood inlet including a first tubular member extending horizontally from said first lateral side to the input chamber, said first tubular member having a closed distal end and one or more apertures located in the input chamber, said apertures facing the top of the bag; and
 (e) a second blood inlet provided at the second lateral side of the bag, said second blood inlet including a second tubular member extending from said second lateral side horizontally into the input chamber, said second tubular member having a closed distal end and one or more apertures located in the input chamber, said apertures facing the top of the bag.

\* \* \* \* \*